US 6,689,139 B2

(12) United States Patent
Horn

(10) Patent No.: US 6,689,139 B2
(45) Date of Patent: Feb. 10, 2004

(54) LONG OBLIQUE ULNA SHORTENING OSTEOTOMY JIG

(76) Inventor: Paul C. Horn, 13403 N. Whitehouse Ct., Spokane, WA (US) 99208

( * ) Notice: Subject to any disclaimer, the term of this patent is extended or adjusted under 35 U.S.C. 154(b) by 0 days.

(21) Appl. No.: 10/075,237

(22) Filed: Feb. 15, 2002

(65) Prior Publication Data

US 2003/0158558 A1 Aug. 21, 2003

(51) Int. Cl.[7] .................................................. A61F 5/00
(52) U.S. Cl. .......................................... 606/87; 606/86
(58) Field of Search .............................. 606/87, 88, 89, 606/96, 97, 98, 86, 53

(56) References Cited

U.S. PATENT DOCUMENTS

| | | | |
|---|---|---|---|
| 5,413,579 A | 5/1995 | Tom Du Toit | 606/87 |
| 5,779,709 A | 7/1998 | Harris, Jr. et al. | 606/87 |
| 5,817,097 A | 10/1998 | Howard et al. | 606/87 |

Primary Examiner—Cary E. O'Connor
Assistant Examiner—Candice C. Melson
(74) Attorney, Agent, or Firm—Richard C. Litman

(57) ABSTRACT

An ulnar osteotomy jig and method for use of said jig for the correction of ulnar impaction syndrome. The jig in cross section is shaped substantially like a right triangle. It has a flat top, a concave bottom which is adapted to closely conform to the surface of an ulna, two flat leg surfaces, and a flat hypothenuse surface. Two holes are defined in the jig and extend between the top and bottom surfaces. When in use, the jig is secured to an ulna with two surgical screws which pass through the holes defined in the jig. A surgeon cuts the ulna with a bone saw into two pieces using the hypothenuse side of the jig as a guide. The two cut ends of the ulna pieces will be repositioned, thereby adjusting the ulna to the proper length and the ulnar pieces will then be secured together with surgical screws.

3 Claims, 5 Drawing Sheets

LONG OBLIQUE ULNA SHORTENING OSTEOTOMY JIG

BACKGROUND OF THE INVENTION

1. Field of the Invention

The present invention relates to surgical instruments and the use thereof, in particular to an ulna cutting jig and its method of use as a guide for obliquely cutting an ulna during surgery to correct ulnar impaction syndrome.

2. Description of the Related Art

There are a variety of surgical instruments present in the art which are designed to guide surgeons when cutting and shaping bone. Due to the unique nature of the human body, surgical instruments often must be specifically designed for particular surgical procedures. Currently there are no known surgical instruments designed for the present novel method of ulnar impaction surgery.

The long oblique ulna shortening osteotomy (LOUSO) jig is an improvement on the current state of the art treatment for ulnar impaction syndrome. Ulnar impaction syndrome is a condition in which the ulna bone is longer than the radius bone, resulting in impaction of the carpal bones on the distal end of the ulna at the wrist joint. Without surgery this condition will lead to the wearing away of the cartilage between the ulna bone and several carpal bones, causing permanent arthritis.

The current surgical technique for correcting ulnar impaction syndrome is referred to as the plating technique and calls for the removal of a wafer of bone, e.g., a disk shaped section of bone, from the ulna, thereby shortening the overall length of the bone. The two remaining pieces of ulna must then be pulled together and secured with a plate spanning the cut which is affixed to the proximal and distal ulnar pieces with several screws.

There are several significant drawbacks with the plating technique. First, the wafer must be exactly the thickness of the desired amount of shortening. Any sizing mistakes are exceedingly difficult, if not impossible, to correct. Second, healing can be unreliable due to the short cross-section and small surface area of bone that must knit together. Insufficient healing can result in long periods of disability, and at times a second surgery involving a bone graft from the pelvis to stimulate bone regrowth. Third, the plate used to secure the ulna together after surgery is often prominent and painful. Many patients require plate removal after the bone has healed. This additional surgery can be expensive, exposes the patient to additional pain and suffering, and the ulna may even fracture during the period of healing after plate removal.

U.S. Pat. No. 5,413,579 discloses a surgical saw guide and drill guide. The saw guide differs from the present invention in that the portion of the saw guide that actually guides a saw blade is very thin as opposed to the guide surface on the present invention, which has much thicker guide surface and provides a much more accurate cut. The '579 saw guide has a seat formation which is formed by a semicylindrical channel, or a portion of semicylindrical channel, having a convex outer side and a concave interior surface, whereas the present invention is formed from a rectangular block with a concave surface milled to conform to the bone and with an oblique cut defining a triangular shape and providing a relatively thick guide surface for the saw blade. The present invention is also specifically designed to attach to the human ulna, and to guide a surgeon when making oblique cuts in the ulna. whereas the saw guide in the '579 patent is designed to correct angular deformities in tubular bones. The '579 invention is not designed, as is the present invention, to extend past the edge of the bone to be cut. This extended portion insures a straight cut all the way through the bone.

U.S. Pat. No. 5,779,709 discloses an ulnar alignment system. This system is designed to provide precision cuts in the proximal portion of the ulna in order to assist in total elbow arthroplasty. The '709 patent is distinguishable because it cannot be used to perform the oblique cuts needed to correct ulnar impaction syndrome using the apparatus and method of the present invention.

U.S. Pat. No. 5,817,097 discloses a bone saw blade guide with a magnet. This device is designed to allow a surgeon to produce precision cuts on the distal end of a femur when performing a knee replacement operation. The bone saw blade guide disclosed in this invention cannot be adapted to produce the oblique cuts on a ulna that are made possible with the present invention.

None of the above inventions and patents, taken either singularly or in combination, is seen to describe the instant invention as claimed. Thus, a long oblique ulna shortening osteotomy jig solving the aforementioned problems is desired.

SUMMARY OF THE INVENTION

The long oblique ulna shortening osteotomy (LOUSO) jig has a flat top surface which is shaped like a substantially right triangle, a concave bottom surface which is also shaped like a substantially right triangle, a flat hypothenuse side surface, and two flat leg side surfaces. The jig has two holes defined therein extending from the top surface to the bottom surface.

The jig is used in connection with a novel method of ulnar impaction corrective surgery. The first step of the surgical method involves securing the jig to the ulna being resized. The concave bottom surface of the jig rests against the corresponding convex surface of the ulna. The jig is secured to the ulna through the use of two surgical screws.

The next step in the surgical method is that the ulna must be severed with a single long oblique cut. The flat hypothenuse side surface of the jig is used to guide a surgical bone saw while making the long oblique cut to insure that the cut is perfectly straight.

Once the cut is made the ulna will be rendered into proximal and distal pieces. The distal piece will then be moved toward the proximal piece with the cut portions sliding past one another such that the overall length of the ulna is reduced by an amount sufficient to correct the ulnar impaction. The proximal and distal ulnar pieces will then be affixed to one another using a number of surgical screws positioned along the cut portion.

Accordingly, it is a principal object of the invention to provide a device and method of use of the device which functions to allow a surgeon to accurately produce a single long oblique cut across the ulna in a surgical procedure to correct ulnar impaction syndrome.

It is another object of the invention to provide a device and method of using the device which will allow for a quicker recovery from ulnar impaction syndrome surgery than conventional methods.

It is a further object of the invention to provide a device and method using the device which functions to obviate the need for a plate to secure the proximal and distal portions of the ulna after surgery for correction of ulnar impaction syndrome.

Still another object of the invention is to provide a surgical device and method of using the device which will function to allow for a diminished risk of infection and more consistent positive results in surgery for repair of ulnar impaction.

It is an object of the invention to provide improved elements and arrangements thereof for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
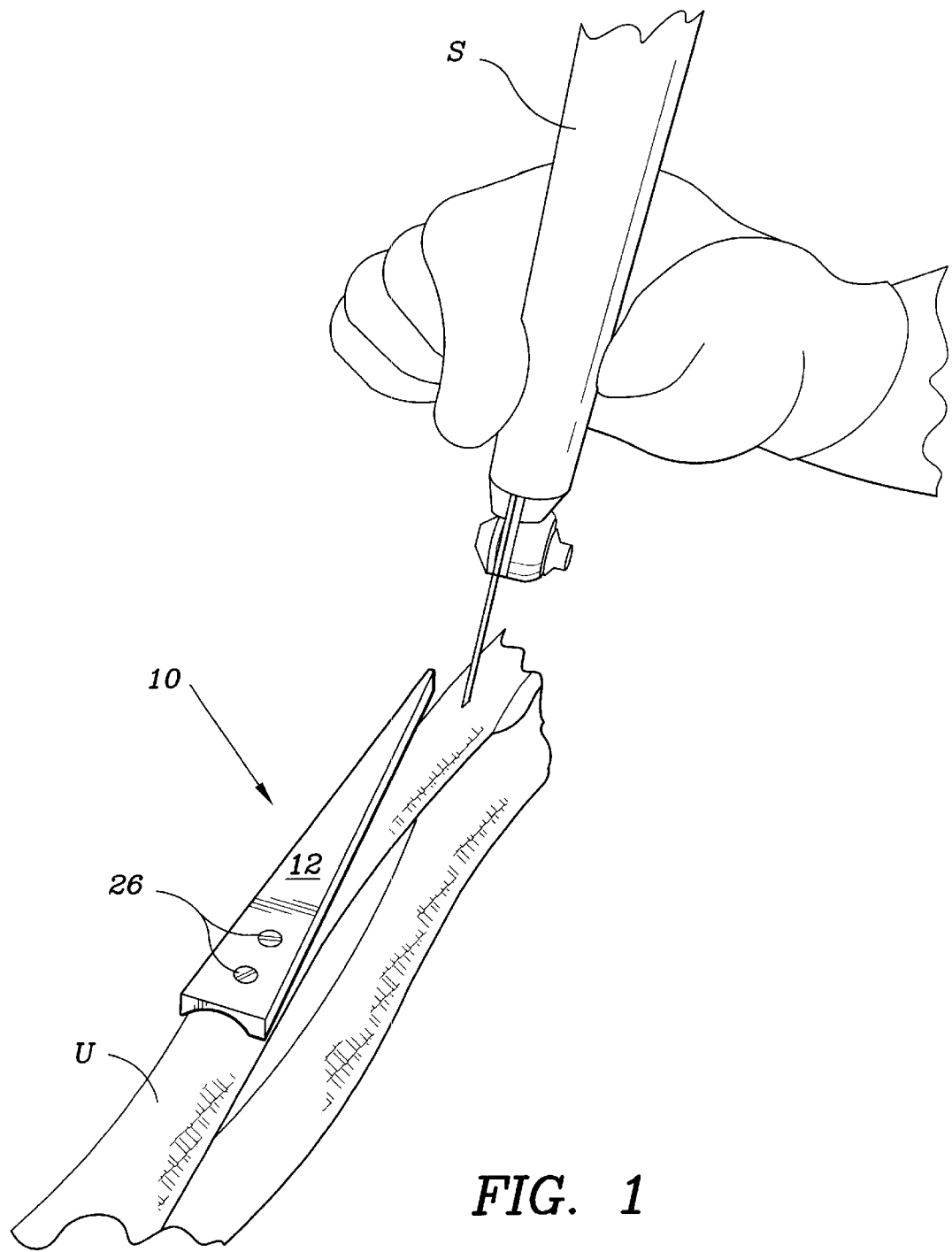
FIG. 1 is an environmental, perspective view of a long oblique ulna shortening osteotomy jig according present invention.
Figure 2:
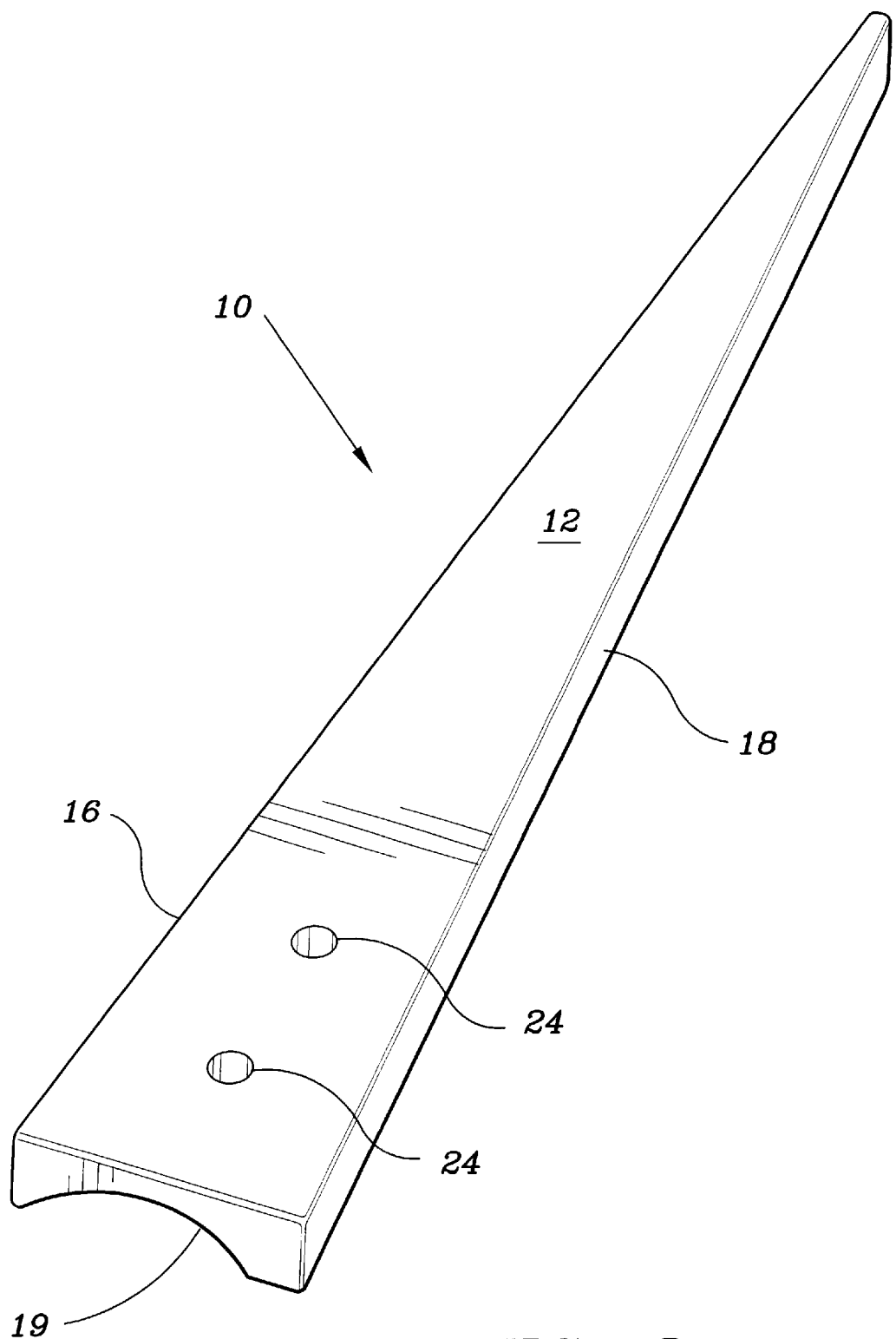
FIG. 2 is a top perspective view of a long oblique ulna shortening osteotomy jig according present invention.
Figure 2A:
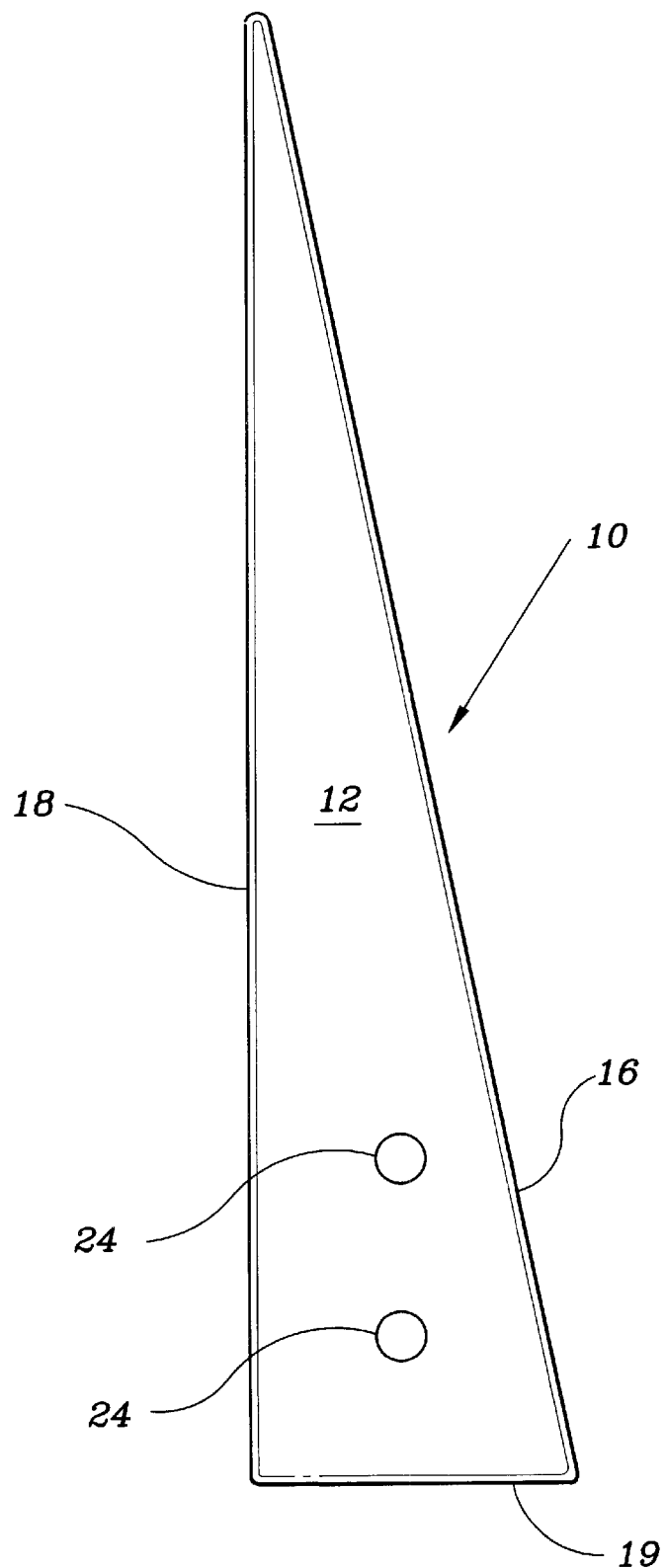
FIG. 2A is top plan view of a long oblique ulna shortening osteotomy jig according present invention.
Figure 3:
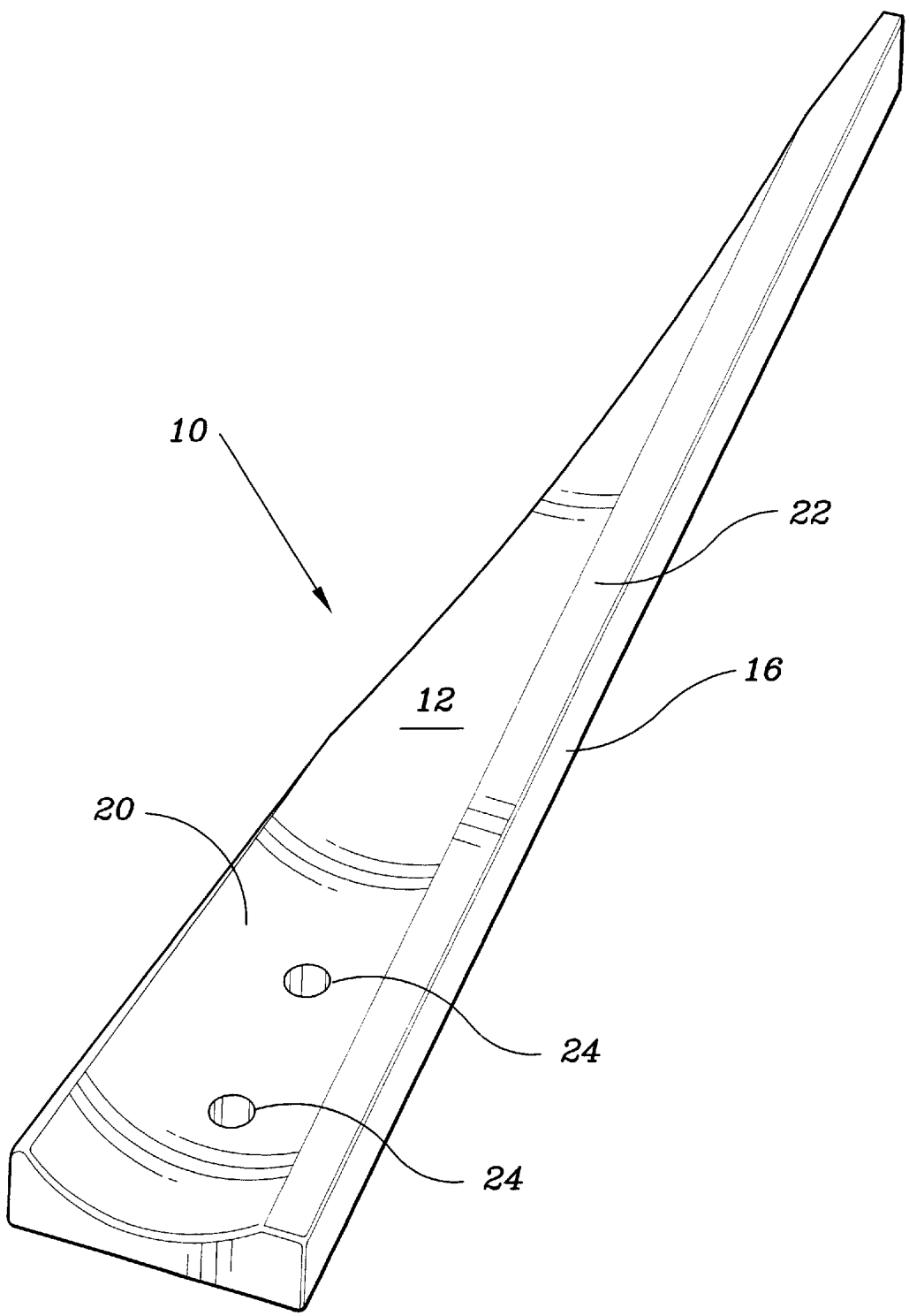
FIG. 3 is a bottom perspective view of a long oblique ulna shortening osteotomy jig according present invention.

The present invention, the long oblique ulna shortening osteotomy (LOUSO) jig, is used to correct ulnar impaction syndrome. The jig 10, as pictured in FIG. 1, is designed to attach to the human ulna U and is shaped like a substantially right triangle in longitudinal cross-section. As seen in FIGS. 2 and 2A the jig 10 has a flat top surface 12, two flat leg side surfaces 16, 19 and a flat hypothenuse side surface 18. The bottom surface 20 of the jig 10, as shown in FIG. 3, is substantially concave except for a 3 mm wide strip 22 which is immediately adjacent to the longer leg 16 and runs the entire length of the jig 10. The concave bottom surface 20 is adapted to conform to the convex surface of an ulna bone U. Two holes 24 are defined in the jig 10 extend between the top surface 12 and the concave bottom surface 20 of the jig 10.

The jig 10 is used in connection with a novel method of ulnar impaction corrective surgery. The first step of the surgical method involves securing the jig 10 to the ulna U being resized. As shown in FIG. 1 the concave bottom surface 20 of the jig rests against the corresponding convex surface of the ulna U. This allows the flat portion of the bottom surface 22 to extend past the outer edge of the ulna U, which provides a stable cutting support surface (discussed below).

The jig 10 is secured to the ulna U through the use of two surgical screws 26. These screws 26 pass through the two holes 24 defined in the jig 10 and are secured in the ulna U.

The next step in the surgical method is that the ulna U is severed with a single long oblique cut. An oblique cut is meant to mean a transverse cut which is not substantially normal to the longitudinal direction of the bone. The flat hypothenuse side surface 18 of the jig 10 is used to guide a bone saw, such as a sag saw S, when making the long oblique cut. Sag saws such as those manufactured under the trade name Stryker are well known in the medical arts, but are not the only type of bone saw capable of preforming this procedure. The jig 10 is designed to overhang one side of the ulna U. This overhang 17 allows the sag saw to be guided throughout the entire cut. Support throughout the entire cut helps insure a completely straight cut, which simplifies the resizing of the ulna and the healing process.

Figure 4:
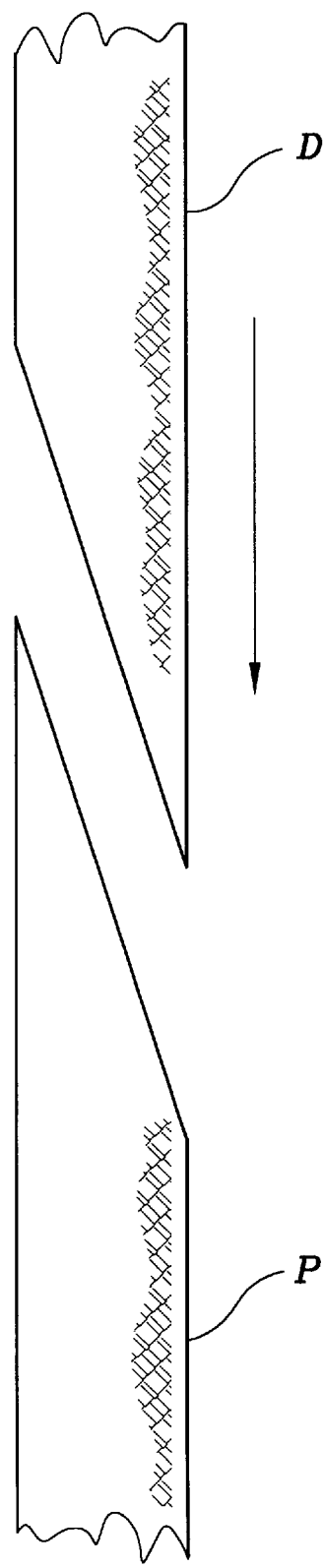
FIG. 4 is an elevation view of a portion of an ulna with an oblique cut.
Figure 5:
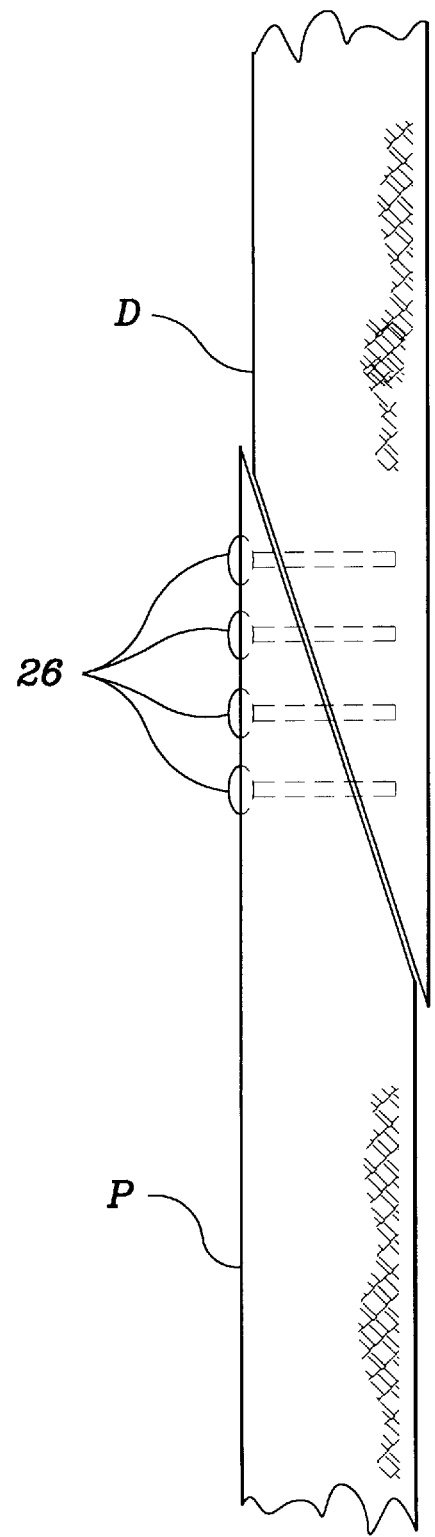
FIG. 5 is an elevation view of a portion of a surgically repaired ulna.

Once the cut is made, the ulna U is rendered into proximal P and distal D pieces as shown in FIG. 4, and the jig 10 is removed. The distal D piece of the ulna is then moved toward the proximal piece P in the direction of the arrow. The proximal P and distal D pieces of ulna, as shown in FIG. 5, are then positioned against one another in an offset manner such that the overall length of the ulna is reduced by an amount sufficient to alleviate the ulnar impaction. A skilled surgeon would be capable of determining the necessary amount of ulnar shortening.

Once the desired ulnar length is achieved, the proximal P and distal D ulnar pieces are affixed to one another using a number of surgical screws 26 positioned along the cut portion of the ulna U. The screws 26 are countersunk to avoid any irritation of surrounding tissue.

The method of the present invention represents an improvement upon conventional ulnar impaction corrective surgery, in which a cylindrical disk or wafer is removed from the ulna U, in that the oblique cut allows the surgeon to adjust the amount of shortening, avoiding the problem of sizing the wafer to be removed. The oblique cut quadruples the surface area of healing bone as compared to the transverse cut in conventional surgery, thereby providing for rapid and solid healing. Countersinking the screw heads 26 in the ulna U obviates the need for subsequent surgery for removal of the screws 26. The overall result is a shorter surgical time with better healing, diminished risk of infection and complications, and decreased expense.

The jig 10 is preferably made from a rectangular block of stainless or surgical steel by milling a concave recess in the bottom surface 20 and making an oblique cut across the block to define the right triangular shape.

It is to be understood that the present invention is not limited to the embodiment described above, but encompasses any and all embodiments within the scope of the following claims.

I claim:

1. A long oblique ulna shortening osteotomy jig, comprising:

a jig body having a longitudinal cross-section shaped like a substantially right triangle, a flat top surface, a concave bottom surface adapted to closely conform to the surface of an ulna bone, a flat hypothenuse side surface, a first flat leg side surface, a second flat leg side surface and two holes defined between the top surface and the bottom surface.

2. A long oblique ulna shortening osteotomy jig according to claim 1, further comprising:

a flat portion adjacent to one leg on the bottom surface of said jig body;

whereby said flat surface is adapted to overhang the edge of a bone when said jig is attached to the bone.

3. A method of surgically correcting ulnar impaction syndrome, comprising the steps of:

a) providing a jig having a longitudinal cross-section shaped like a substantially right triangle, a flat top surface, a concave bottom surface adapted to closely conform to the surface of an ulna bone, a flat hypothenuse side surface, a first flat leg side surface, a second flat leg side surface and two holes defined through the jig and extending between the top surface and the bottom surface;

b) placing the bottom surface of said jig securely against the ulna to be operated on with the concave bottom surface conforming to the surface of the ulna;

c) securing said jig to the ulna with two surgical screws positioned in the holes defined in said jig;

d) obliquely cutting said ulna into two pieces with a bone saw using the hypothenuse side of said jig as a cutting guide;

e) removing said jig from the ulna;

f) sliding the two pieces of the ulna past one another such that the overall length of the ulna is shortened to alleviate the symptoms of ulnar impaction syndrome; and g) securing the pieces of said ulna together with a plurality of countersunk surgical screws.

\* \* \* \* \*